United States Patent
Jennings

(10) Patent No.: US 7,083,602 B1
(45) Date of Patent: Aug. 1, 2006

(54) FLOSSING KIT FOR CLEANING PIERCED BODY PARTS

(76) Inventor: Bina R. Jennings, 5745 E. 4th Ter., Tulsa, OK (US) 74112

( * ) Notice: Subject to any disclaimer, the term of this patent is extended or adjusted under 35 U.S.C. 154(b) by 278 days.

(21) Appl. No.: 10/675,337

(22) Filed: Sep. 30, 2003

(51) Int. Cl.
*A61M 35/00* (2006.01)

(52) U.S. Cl. ........................... 604/289; 604/289

(58) Field of Classification Search ............... 604/289, 604/1–3; 132/309; 427/2.29
See application file for complete search history.

(56) References Cited

U.S. PATENT DOCUMENTS

| | | | |
|---|---|---|---|
| 4,041,946 A | 8/1977 | Barton | |
| 4,497,402 A | 2/1985 | Karos | |
| 4,519,408 A * | 5/1985 | Charatan | 132/321 |
| 4,798,216 A | 1/1989 | McCarty et al. | |
| D346,443 S | 4/1994 | Franklin | |
| 5,954,682 A * | 9/1999 | Petrus | 604/1 |
| 6,146,398 A | 11/2000 | Satterfield | |
| 6,358,221 B1 | 3/2002 | Waters et al. | |

* cited by examiner

*Primary Examiner*—Tatyana Zalukaeva
*Assistant Examiner*—Ginger Chapman

(57) ABSTRACT

A kit for cleaning pierced body parts includes a floss formed to be flexible and including a plurality of perforations spaced along a length thereof for assisting a user to separate the floss at the perforations. The kit further includes an applicator formed to be substantially tubular and having open, opposed end portions for passing the floss therethrough. The kit further includes a sterilizing substance coated on the inner surface of the applicator and transferable onto the floss as same passes through the applicator so that a pierced body part may be cleaned as the floss is passed therethrough. The sterilizing substance preferably includes peroxide, antibiotic ointment and/or alcohol. A dispenser for housing the floss and having an aperture formed therein, allows the floss to be selectively removed therefrom.

9 Claims, 2 Drawing Sheets

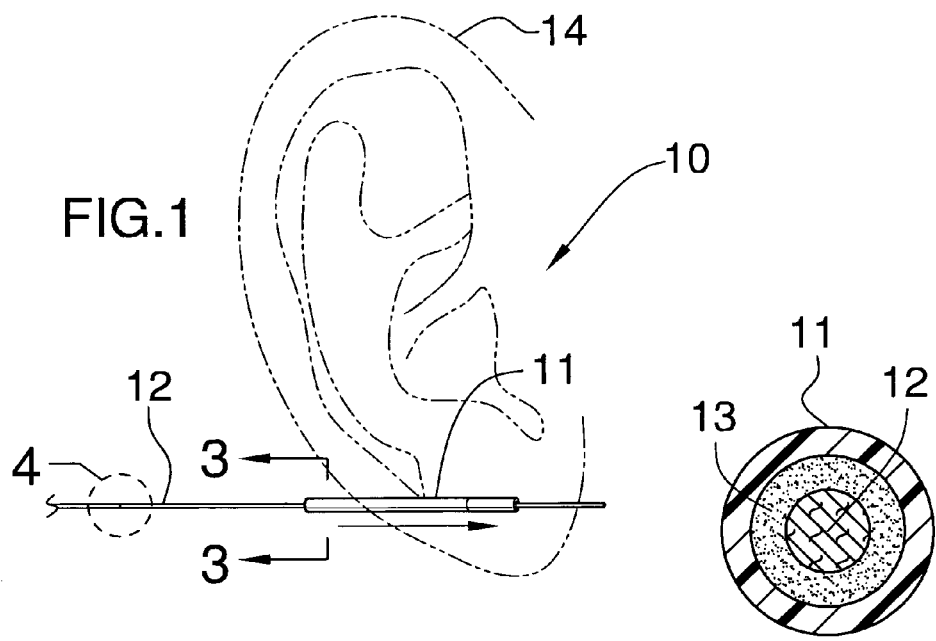
FIG.1
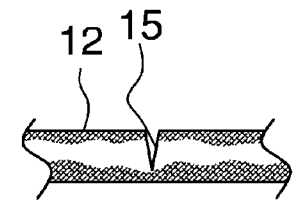
FIG.3
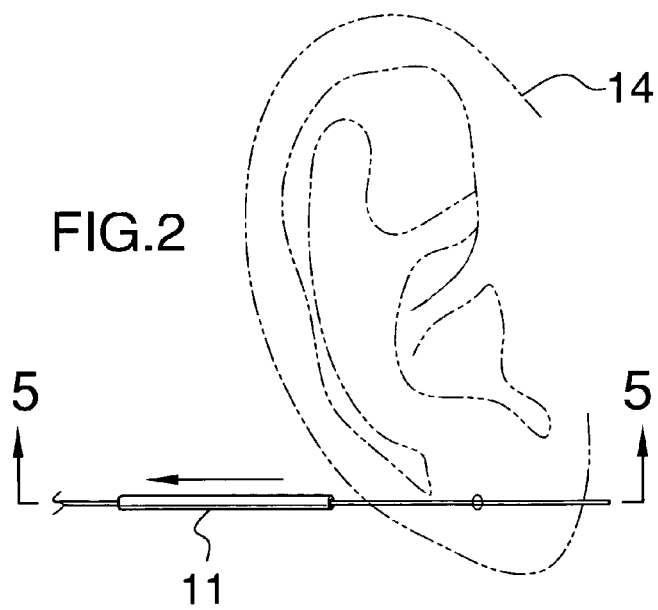
FIG.2
FIG.4

FLOSSING KIT FOR CLEANING PIERCED BODY PARTS

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to a kit for cleaning pierced body parts and, more particularly, to a flossing kit including an applicator for coating floss with a disinfectant as the floss passes through the applicator.

2. Prior Art

Body piercing has been a long established practice in all countries and cultures. This practice has been manifest in the use of a wide variety of techniques and procedures involving numerous locations on the human body and various sizes of piercing to these sites.

Perhaps the most common and least painful example of body piercing involves piercing of the lower earlobe. Body piercing, however, has become more prevalent and widely accepted among the general population. It has become commonplace for individuals, especially those under twenty years of age in Western Countries, to have body piercing to the eyebrows, chin, lower as well as upper ear ridge, nose, mouth, tongue, navel, nipples, and even more private parts of the body.

Though the practice of body piercing has been around for centuries, people have traditionally experienced some health complications related to this practice. Complications most often are due to the absence of a suitable sterile environment, e.g., using piercing tools or instruments that are not sterile, or the insertion of non-sterile or contaminated appliances, rings, hooks, or whatever device or product is inserted into the pierced cavity, and poor hygiene.

Soreness, bacterial infections and closure of the desired pierced opening result from contamination and the absence of a proper sterile and aseptic cleaning method and kit. Bacterial action results from contamination of sensitive and difficult to get to portions of the body where body piercing has occurred. The removal of foreign matter and particles and the observance of sterile techniques promote more healthy skin tissue and reduce the incidence of infections, irritation, and soreness. Accordingly, maintaining clean and healthy tissue in pierced sites is important to one's overall good health.

BRIEF SUMMARY OF THE INVENTION

In view of the foregoing background, it is therefore an object of the present invention to provide a flossing kit for cleaning pierced body parts. These and other objects, features, and advantages of the invention are provided by a kit including a floss formed to be flexible and including a plurality of perforations spaced along a length thereof for, assisting a user to separate the floss at the perforations.

The kit further includes an applicator formed to be substantially tubular and having opposed end portions for passing the floss therethrough. The applicator includes a longitudinal axis and an inner surface substantially equally spaced thereabout. The applicator preferably has a substantially cylindrical shape and the opposed end portions are open and preferably have substantially equal diameters.

The kit further includes a sterilizing substance coated on the inner surface of the applicator and transferable onto the floss as same passes through the applicator so that a pierced body part may be cleaned as the floss is passed therethrough. The sterilizing substance preferably includes peroxide, antibiotic ointment and/or alcohol. A dispenser for housing the floss and having an aperture formed therein, allows the floss to be selectively removed therefrom. The kit may further include a packaging for housing the floss therein.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a perspective view showing a kit for cleaning pierced body parts, in accordance with the present invention;

FIG. 2 is a perspective of FIG. 1 wherein the applicator tube has been removed from the pierced body part thereby allowing the floss to clean the piercing;

FIG. 3 is an enlarged cross-sectional view taken along line 3—3 in FIG. 1;

FIG. 4 is an enlarged cross-sectional view taken along line 4—4 in FIG. 1;

DETAILED DESCRIPTION OF THE INVENTION

Figure 5:
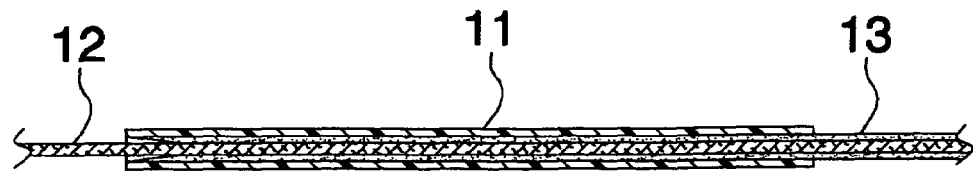
FIG. 5 is an enlarged cross-sectional view taken along line 5—5 in FIG. 2.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art.

The kit of this invention is referred to generally in FIGS. 1 and 2 by the reference numeral 10 and is intended to provide a combined floss and applicator for cleaning pierced body parts. It should be understood that the kit 10 may be used to clean various pierced body parts and therefore should not be construed as limited to cleaning only pierced ear lobes.

The kit 10 includes an applicator 11 having a substantially cylindrical shape and a longitudinal axis passing therethrough. The inner surface of the applicator 11 is substantially equally spaced about the longitudinal axis and is coated with a sterilizing or disinfecting substance 13 for cleaning pierced body parts, as perhaps best shown in FIG. 3. Such a disinfectant 13 may be formed from alcohol, antibiotic ointment, peroxide and other conventional sterilizing substances, as well known in the art.

A floss 12 formed to be flexible includes a plurality of perforations 15 selectively spaced along a length of thereof, as perhaps best shown in FIG. 4. Such perforations 15 allow a user to easily separate the floss 12 at predetermined lengths. Such a floss 12 may be a conventional floss having a wax coating or being made from suitable material for absorbing the sterilizing substance 13 as the floss 12 is passed through the applicator 11. Of course, such an applicator is preferably small enough in diameter so that it can be inserted into a pierced body part 14 and thereby guides the floss 12 therethrough.

Now referring to FIG. 5, it can be seen that as the floss 12 is passed through the opposed end portions of the applicator 11, the floss 12 becomes coated with the sterilizing substance 13. Advantageously, the floss 12 does not need to be pre-coated with such substance 13 when it is packaged. Of course, a plurality of applicators 11 may be included in the kit 10 so that each applicator 11 may be discarded after use.

Figure 6:
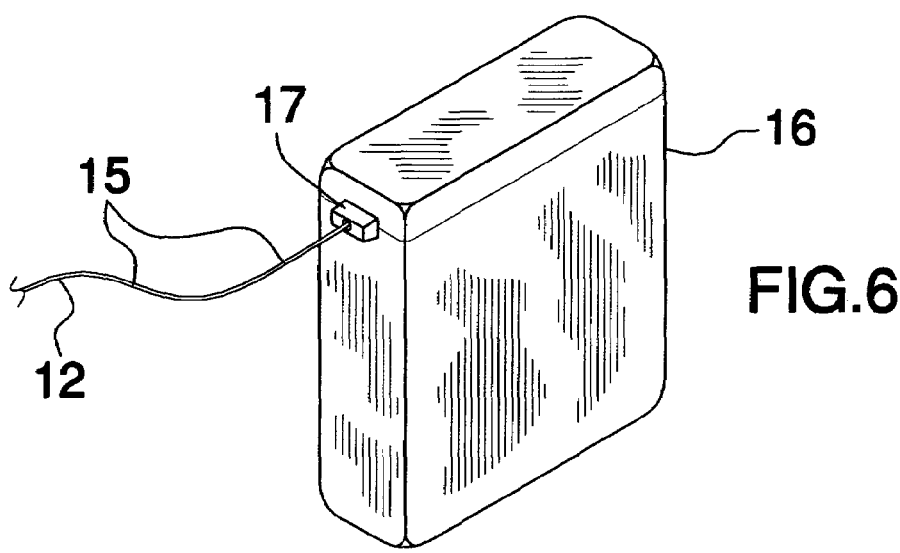
FIG. 6 is a perspective view showing a floss dispenser, in accordance with the present invention.
Figure 7:
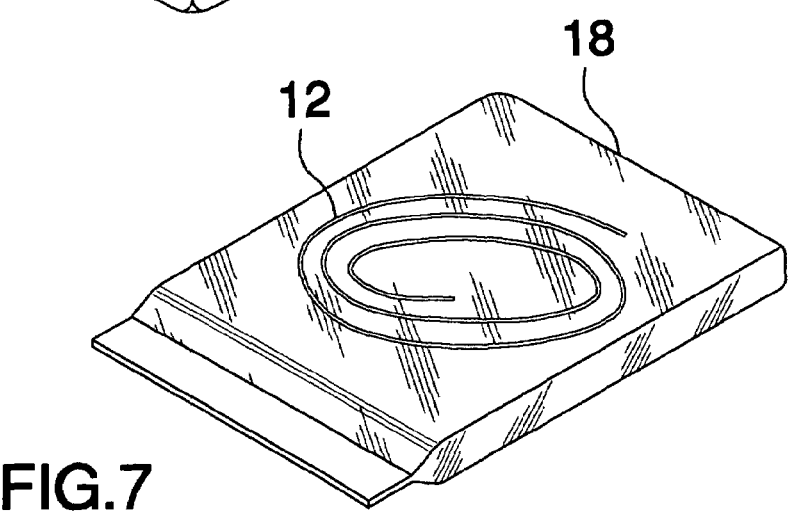
FIG. 7 is a perspective view showing a floss packaging.

Now referring to FIG. 6, the kit 10 may also include a conventional dispenser 16 having an aperture 17 formed at a top portion thereof and for allowing a user to selectively remove the floss 12 therefrom and separate same at its perforations 15. Alternately, the kit 10 may include a package 18 which houses the floss 12 and applicators 11 therein, as shown in FIG. 7.

In operation, a user simply removes a predetermined amount of floss 12 from the dispenser 17 or packaging 18 and passes same through an applicator 11. The applicator 11 is then passed through a pierced body part and the forward end of the floss 12 is pushed outwardly from the applicator 11. Now, as the applicator 11 is gently removed from the pierced body part, it leaves behind the floss 12 disposed through the pierced body part. The opposed ends of the floss 12 can be grasped and twisted to thoroughly clean the pierced body part. After cleaning, the floss 12 and its associated applicator 11 can be discarded.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed is:

1. A kit for cleaning pierced body parts and comprising:
   a floss formed to be flexible and including a plurality of perforations spaced along a length thereof and for assisting a user to separate said floss at said perforations;
   a plurality of applicators formed to be substantially tubular and having opposed end portions for passing said floss therethrough, said plurality of applicators including a longitudinal axis and an inner surface substantially equally spaced thereabout, said plurality of applicators having a substantially cylindrical shape, said opposed end portions being open and having substantially equal diameters;
   a sterilizing substance coated on said inner surface and being transferable onto said floss as same passes through said plurality of applicators respectively so that a pierced body part may be cleaned as said floss is passed therethrough; and
   a dispenser for housing said floss and having an aperture formed therein for allowing said floss to be selectively removed therefrom.

2. The kit of claim 1, further comprising a packaging for housing said floss therein.

3. The kit of claim 1, wherein said sterilizing substance comprises antibiotic ointment.

4. The kit of claim 1, wherein said sterilizing substance comprises peroxide.

5. The kit of claim 1, wherein said sterilizing substance comprises alcohol.

6. A kit for cleaning pierced body parts and comprising:
   a floss formed to be flexible and including a plurality of perforations spaced along a length thereof and for assisting a user to separate said floss at said perforations;
   a plurality of applicators formed to be substantially tubular and having opposed end portions for passing said floss therethrough, said plurality of applicators including a longitudinal axis and an inner surface substantially equally spaced thereabout, said plurality of applicators having a substantially cylindrical shape, said opposed end portions being open and having substantially equal diameters;
   a sterilizing substance coated on said inner surface and being transferable onto said floss as same passes through said plurality of applicators respectively so that a pierced body part may be cleaned as said floss is passed therethrough; and
   a dispenser for housing said floss and having an aperture formed therein for allowing said floss to be selectively removed therefrom;
   wherein said perforations traverse across a width of said string and are oriented perpendicular to a longitudinal length of said string.

7. The kit of claim 6, wherein said sterilizing substance comprises antibiotic ointment.

8. The kit of claim 6, wherein said sterilizing substance comprises peroxide.

9. The kit of claim 6, wherein said sterilizing substance comprises alcohol.

* * * * *